US009498354B2

(12) United States Patent
Cook

(10) Patent No.: US 9,498,354 B2
(45) Date of Patent: Nov. 22, 2016

(54) ACTUATION SYSTEM FOR A JOINT

(71) Applicant: Milwaukee School of Engineering, Milwaukee, WI (US)

(72) Inventor: Douglas Lee Cook, Milwaukee, WI (US)

(*) Notice: Subject to any disclaimer, the term of this patent is extended or adjusted under 35 U.S.C. 154(b) by 358 days.

(21) Appl. No.: 14/209,849

(22) Filed: Mar. 13, 2014

(65) Prior Publication Data

US 2014/0260950 A1 Sep. 18, 2014

Related U.S. Application Data

(60) Provisional application No. 61/851,750, filed on Mar. 13, 2013.

(51) Int. Cl.
| | |
|---|---|
| *A61F 2/68* | (2006.01) |
| *A61H 1/02* | (2006.01) |
| *A61H 3/00* | (2006.01) |
| *A61F 2/60* | (2006.01) |
| *A61F 2/70* | (2006.01) |
| *A61F 2/74* | (2006.01) |

(52) U.S. Cl.
CPC . *A61F 2/68* (2013.01); *A61H 1/02* (2013.01); *A61H 1/0266* (2013.01); *A61H 3/00* (2013.01); *A61F 2/60* (2013.01); *A61F 2002/702* (2013.01); *A61F 2002/741* (2013.01); *A61F 2002/748* (2013.01); *A61H 2201/1246* (2013.01); *A61H 2201/149* (2013.01); *A61H 2201/1671* (2013.01)

(58) Field of Classification Search
CPC ............ A61F 2002/748; A61F 2002/74; A61F 2/68; A61H 2201/1671
See application file for complete search history.

(56) References Cited

U.S. PATENT DOCUMENTS

| | | | |
|---|---|---|---|
| 4,873,948 A | 10/1989 | Richeson et al. | |
| 5,074,192 A | 12/1991 | Gheorghita | |
| 6,223,648 B1 * | 5/2001 | Erickson | F15B 15/103 92/92 |
| 6,645,252 B2 * | 11/2003 | Asai | A61F 2/68 623/24 |
| 7,571,699 B2 | 8/2009 | Forner, Sr. et al. | |
| 8,051,764 B2 * | 11/2011 | Jacobsen | F15B 11/16 91/519 |

(Continued)

OTHER PUBLICATIONS

Li, Y., Morris, E.A., Shorter, K.A., and Hsiao-Wecksler, E.T. "Energy Efficiency Analysis of a Pneumatically-Powered Ankle-Foot Orthosis," Proceedings of the 52nd National Conference on Fluid Power. Las Vegas, Nevada (2011).

(Continued)

*Primary Examiner* — Thomas E Lazo
(74) *Attorney, Agent, or Firm* — Roy L. Chan, A Professional Law Corporation

(57) ABSTRACT

An actuation system for a joint includes an actuator having a piston, an articulating element coupled to the actuator that is driven by the piston to match a gait cycle of an appendage, an energy source engaged with the piston that energizes working fluid within the actuator to drive the piston and generate exhaust gas, a plurality of valves coupled to the actuator, and an exhaust gas holding element coupled to the actuator that is sized to hold a volume of the exhaust gas contained within the actuator.

26 Claims, 16 Drawing Sheets

(56) References Cited

U.S. PATENT DOCUMENTS

| | | | |
|---|---|---|---|
| 8,731,716 B2* | 5/2014 | Jacobsen | A61F 2/68 700/245 |
| 2004/0083007 A1* | 4/2004 | Molino | A61F 2/64 623/26 |
| 2007/0198098 A1* | 8/2007 | Roston | A61F 2/68 623/26 |
| 2012/0289870 A1* | 11/2012 | Hsiao-Wecksler | A61H 1/0266 601/5 |

OTHER PUBLICATIONS

"Plustech Walking Machine," http://gizmodo.com/036148/plustech-walking-machine (2005); see also https://youtu.be/CD2V8GFqk_Y.

Mikell Taylor "Scoop: New video of BDI's Big Dog robot," IEEE Spectrum Inside Technology, 2008 http://spectrum.ieee.org/automaton/robotics/robotics-software/scoop_new_video_of_bdis_big_do.

Marina Levina, "Boston Dynamics Wins DARPA Contract to Develop Legged Squad Support System (LS3)" Carnegie Mellon, 2010 http://www.cs.cmu.edu/~cga/humanoids-ugrad/bdi.pdf.

Richard Remmers, Doug Cook and Vito Gervasi, Custom, Integrated, Pneumatic, Rotary Actuator for an Active Ankle-Foot Orthosis 2010 SFF Symposium Proceedings, http://utwired.utexas.edu/lff/symposium/proceedingsArchive/pubs/Manuscripts/2010/2010-69-Remers.pdf.

Aimin Yang, Junsheng Pu, C.B. Wong, Phillip Moore, "By-Pass Valve Control to Improve Energy Efficiency of Pneumatic Drive System," Control Engineering Practice, vol. 17, pp. 623-628, 2009.

David Winter, "Biomechanics and Motor Control of Human Movement," Chapter 7 on Muscle Mechanics, 2nd Edition, John Wiley & Sons, 1990.

Janice Eng and David Winter, "Kinetic Analysis of the Lower Limbs During Walking: What Information Can Be Gained from a Three-Dimensional Model?" Journal of Biomechanics, vol. 28, No. 6, pp. 753-758, 1995.

Shawn Bongiorno, "Characterization of Design Criteria for Lattice Structures as Sonic Range Acoustic Absorbent Media," Submitted to Journal of Young Investigators, 2011.

* cited by examiner

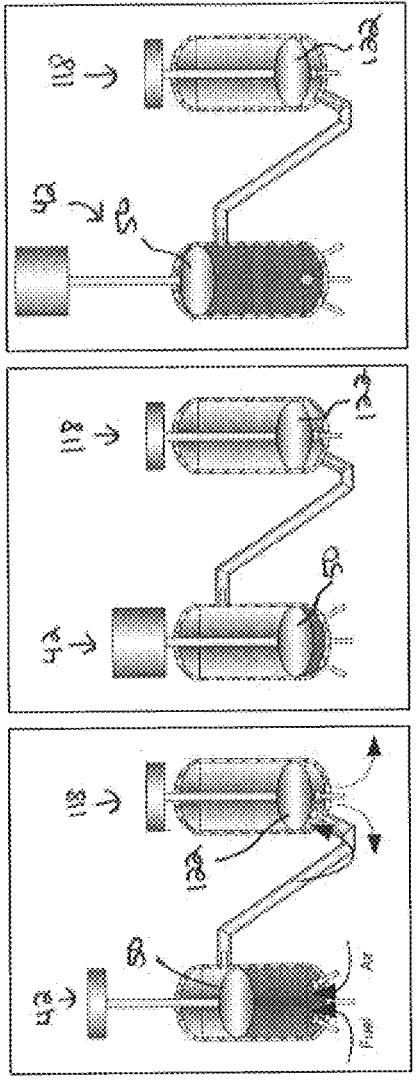
FIG. 6
FIG. 5
FIG. 4
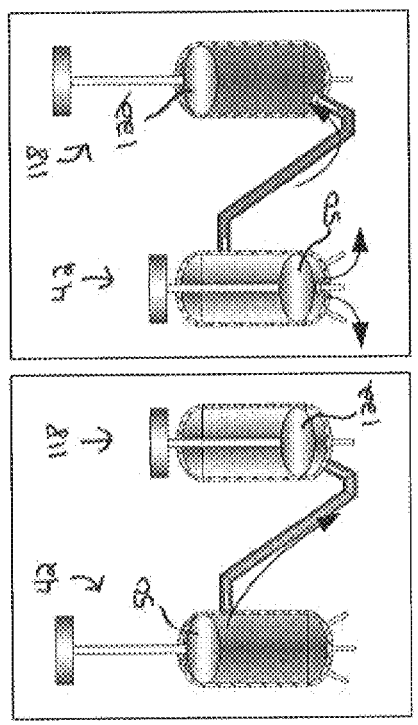
FIG. 8
FIG. 7

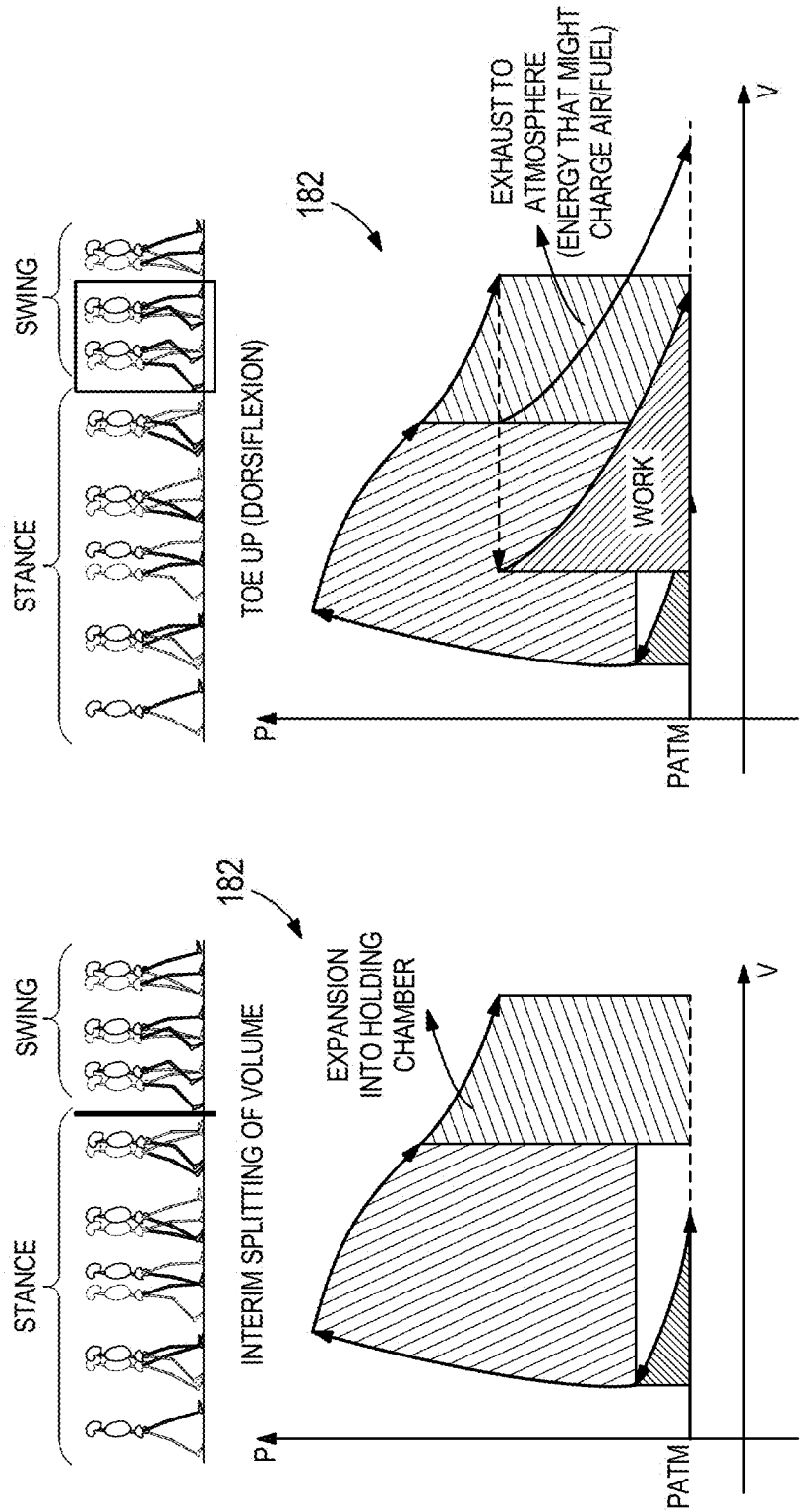

ACTUATION SYSTEM FOR A JOINT

CROSS-REFERENCE TO RELATED APPLICATIONS

This application is a non-provisional of and claims priority to U.S. Provisional Application No. 61/851,750, filed Mar. 13, 2013, the entire contents of which are incorporated herein by reference.

BACKGROUND OF THE INVENTION

Some actuation systems for joints currently utilize battery power to actuate movement of one or more components in the system. However, these systems lose approximately 40% of the battery's stored chemical-potential energy into the atmosphere, primarily as heat, which can lead to faster system degradation and safety issues, particularly when operating in close proximity to humans. Also, due to their lower energy density, small batteries require frequent recharging, which is often impractical, and large, heavy batteries that provide longer operation times consume more of the available energy just to accelerate the additional mass of the battery.

SUMMARY OF THE INVENTION

The present invention relates to an actuation system for a joint, and in particular to a high-efficiency biomimetic articulated joint actuation system.

In one construction, the invention provides an actuation system for a joint that includes an actuator having a piston, an articulating element coupled to the actuator that is driven by the piston to match a gait cycle of an appendage, an energy source engaged with the piston that energizes working fluid within the actuator to drive the piston and generate exhaust gas, a plurality of valves coupled to the actuator, and an exhaust gas holding element coupled to the actuator that is sized to hold a volume of the exhaust gas contained within the actuator.

In another construction, the invention provides a method of using an actuation system for a joint that includes coupling an actuation system to an appendage, the actuation system including a primary actuator and a secondary actuator, the primary and secondary actuators working in dual, opposing motion to one another as the appendage moves through a gait cycle. The method also includes moving a piston within the primary actuator to generate a first actuation movement of an articulating element coupled to the primary actuator, directing exhaust into the second actuator to power a second actuation movement of the articulating element, and matching the gait cycle of the appendage with a thermodynamic cycle of the actuation system.

In another construction, the invention provides a method of harvesting energy with an actuation system for a joint includes coupling an actuation system to an appendage, the actuation system including a primary actuator powered by a mixture of air and fuel. The method also includes pressing a portion of the appendage toward a surface to engage and activate a hydraulic bellows on the actuation system, and injecting air and fuel into the primary actuator with the activated hydraulic bellows.

Other aspects of the invention will become apparent by consideration of the detailed description and accompanying drawings.

BRIEF DESCRIPTION OF THE DRAWINGS

FIGS. 4-8 are schematic illustrations of the actuation system of FIG. 1, with pistons that allow for variable diameters and stroke lengths.

FIGS. 19-24 are diagrams illustrating a thermodynamic cycle for the actuation system of FIG. 1, the thermodynamic cycles matching the gait cycle of human leg.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1:
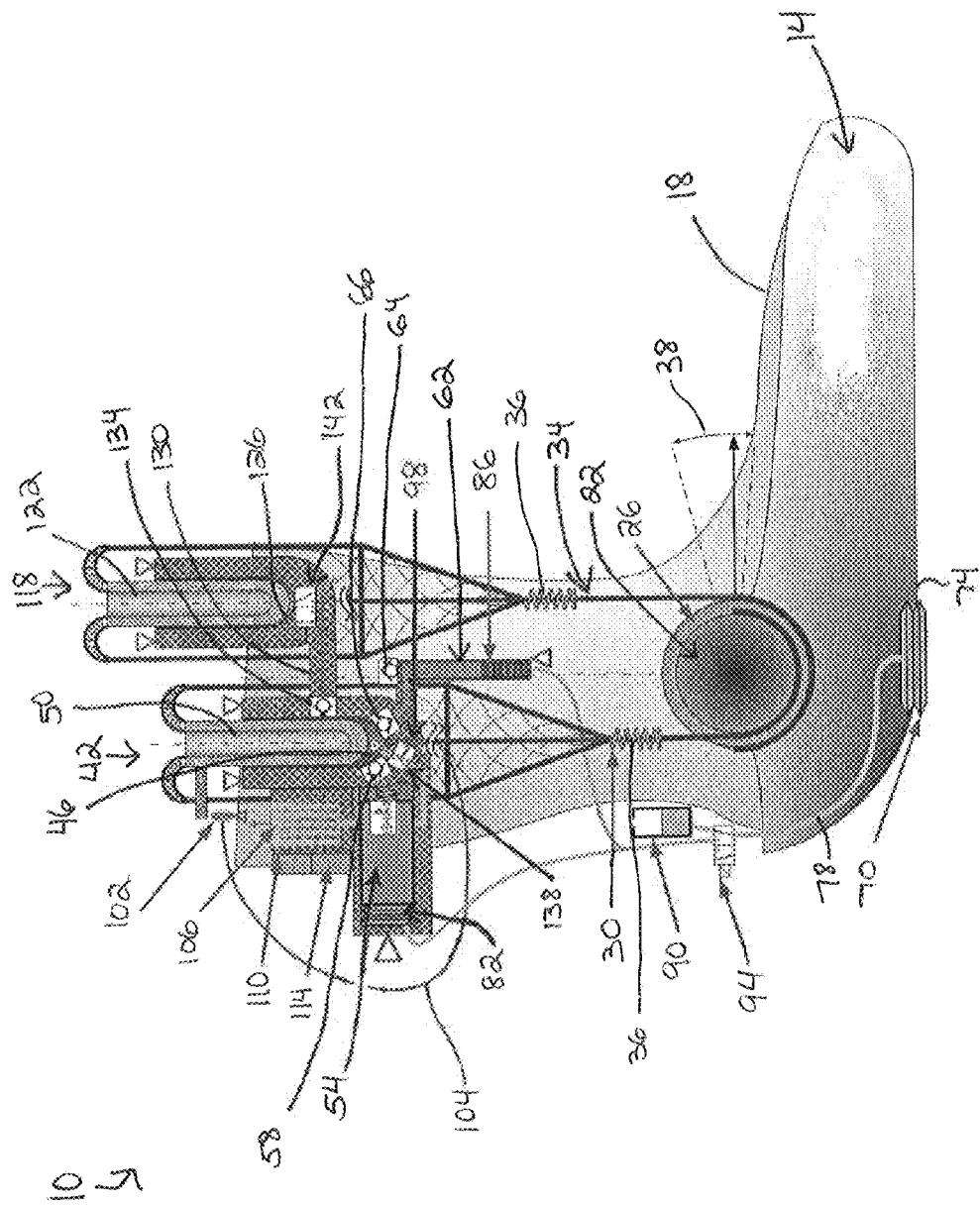
FIG. 1 is a schematic illustration of an actuation system for a joint according to one construction of the invention.

FIG. 1 illustrates an actuation system 10 for a joint. The system 10 includes an articulating component 14. In the illustrated construction, the articulating component 14 is a platform or shoe worn by a user. The articulating component 14 is form-fitted for at least a portion of a foot 18 of the user to fit within the articulating component 14, and provides support for the foot 18 during a gait cycle of the user's leg.

With continued reference to FIG. 1, the system 10 also includes a set of independent pulleys 22, 26 coupled to the articulating component 14, and first and second tension cables 30, 34 coupled to the pulleys 22, 26. The pulleys 22, 26 mimic a pivoting, torsional action of a human ankle, and the tension cables 30, 34 mimic actions of tendons in the human body.

As illustrated in FIG. 1, the tension cable 30, which includes a custom compliance shock and piston extension 36, is coupled to the pulley 22, and the tension cable 34 (which also includes a custom compliance shock and piston extension 36) is coupled to the pulley 26, so that upward movement (i.e., in a direction away from the articulating component 14) of the tension cable 30 generates a first pivoting movement (i.e., plantarflexion) of the articulating component 14, and upward movement of the tension cable 34 generates an opposite pivoting movement (i.e., dorsiflexion) of the articulating component 14, mimicking the natural movement of a human foot during the gait cycle. FIG. 1 further illustrates an example of an angle 38 through which one of the pulleys (i.e., pulley 26) moves.

With continued reference to FIG. 1, the pulleys 22, 26 convert linear force (corresponding to the up and down movement of the tension cables 30, 34) into torque (corresponding to the pivoting action of the articulating component 14). The pulley 26 is separate from the pulley 22, and latches in only one direction. While the pulleys 22, 26 in the illustrated construction are circular, in some constructions the pulleys have radii that change about their axes to optimize torque output with respect to angular position.

With continued reference to FIG. 1, the system 10 also includes a first actuator 42 coupled to the first tension cable 26. The actuator 42 includes a combustion chamber 46 that houses a reciprocating, shaped piston 50 that is coupled to the tension cable 30 (e.g., with the custom compliance shock and piston extension 36). Movement of the piston 50 generates tension within the tension cable 30, which causes the articulating component 14 to swing.

The actuator 42 includes a fuel cartridge 54 coupled to the combustion chamber 46 to deliver fuel (e.g., butane) to the combustion chamber 46. As illustrated in FIG. 1, the fuel passes through a valve 58 into the combustion chamber 46.

The actuator 42 also includes an air injection component 62 coupled to the combustion chamber 46 to deliver air to the combustion chamber 46. As illustrated in FIG. 1, air is drawn in through a valve 64 from the ambient environment, and passes out through a valve 66 into the combustion chamber 46.

To deliver fuel and air into the combustion chamber 46 the illustrated system 10 utilizes harvested energy from movement of the foot 18 and the articulating component 14. In particular, the system 10 includes a heel-strike-harvesting hydraulic bellows pump 70 coupled to a bottom, heel portion 74 of the articulating component 14. The pump 70 is activated (i.e., compressed) when the heel portion 74 strikes a supporting surface (e.g., a floor or ground surface), generating a flow of fluid that moves through a set of conduits 78.

With continued reference to FIG. 1, the conduits 78 deliver at least a portion of the flow of fluid to a hydraulic bellows (or bladder) fuel injector 82 coupled to the fuel cartridge 54, where the energy transferred through the fluid is used to eject fuel from the fuel cartridge 54 through the valve 58 and into the combustion chamber 46.

The conduits 78 also deliver at least a portion of the flow of fluid to a hydraulic bladder 86 in the air injection component 62, where the bladder 86 is used to push (e.g., compress) air disposed within the air injection component 62 and force the air through the valve 66 and into the combustion chamber 46.

With continued reference to FIG. 1, the system 10 includes a hydraulic reservoir 90 and a hydraulic solenoid valve or valves 94 that control whether the flow of fluid from the pump 70 is moved to the hydraulic reservoir 90, or to the fuel injector 82 or bladder 86. Control of the solenoid valve 94 is based on whether the system 10 is in a walking state or a standing state. For example, in the walking state, the valve or valves 94 are opened so that fluid may move to the fuel injector 82 and the bladder 86. In other constructions, the delivery of fuel and air to the combustion chamber 46 is powered with an integrated power source (e.g., a battery), as opposed to being powered by harvested energy.

With continued reference to FIG. 1, the system 10 also includes a spark plug 98 that is coupled to the combustion chamber 46. The spark plug 98 ignites the combined fuel and air mixture that is injected into the combustion chamber 46 by the fuel injector 82 and the air injection component 62, so as to generate combustion within the chamber 46 and drive motion of the piston 50.

In the illustrated construction the system 10 utilizes harvested energy from movement of the articulating component 14 (or the system 10 as a whole) to power the spark plug 98. In particular, the system 10 includes a piezoelectric spark generator 102 that is coupled via a wire 104 to the spark plug 98. As the articulating component 14 (or the system 10 as a whole) moves, the movement generates electricity in the piezoelectric spark generator 102, which then provides power to the spark plug 98. In other constructions, the spark plug 98 is powered with an integrated power source (e.g., a battery), as opposed to being powered by harvested energy.

With continued reference to FIG. 1, the system 10 also includes an exhaust-heat recuperator 106, a thermoelectric generator (TEG) 110, and a phase-change material (PCM) 114, each coupled to the actuator 42. The exhaust-heat recuperator 106, thermoelectric generator 110, and phase-change material 114 provide added power and energy conservation to the system 10. For example, the phase-change material 114 recovers waste heat and supplies it to other regions for greater work production, while also maintaining a safe operating temperature for the user of the system 10.

With continued reference to FIG. 1, the system 10 also includes a second actuator 118 that is coupled to the first actuator 42 and drives movement of the tension cable 34, the pulley 26, and the articulating component 14. The second actuator 118 includes a reciprocating, shaped piston 122 disposed within a piston chamber 126. The reciprocating piston 122 is coupled to the tension cable 34 (e.g., with the custom compliance shock and piston extension 36), such that when the piston 122 moves, the tension cable 34 and pulley 26 also move.

The second actuator 118 is an element that holds a volume of exhaust gas, is coupled to the first actuator 42 with an exhaust line 130, and is driven by exhaust gas from the first actuator 42. As illustrated in FIG. 1, the first actuator 42 includes an exhaust valve 134 that opens into the exhaust line 130, as well as a solenoid pneumatic valve 138 that controls movement of exhaust from the first actuator 42. When the pneumatic valve 138 is closed (e.g., during a walking state), the exhaust from the first actuator 42 is able to pass through the exhaust valve 134 and into the exhaust line 130. When the pneumatic valve 138 is open, exhaust from the first actuator 42 may be expelled into the ambient environment or to one of the exhaust-heat recuperator 106, thermoelectric generator (TEG) 110, and/or phase-change material (PCM) 114.

With continued reference to FIG. 1, the second actuator 118 includes a plurality of pneumatic valves 142 that control whether exhaust from the exhaust line 130 enters the piston chamber 126 or whether exhaust in the piston chamber 126 is expelled into the ambient environment. In the illustrated construction the valves 142 are powered by the thermoelectric generator 110.

When the exhaust from the exhaust line 130 enters the piston chamber 126, the exhaust has sufficient kinetic and/or thermal energy to power movement of the piston 122, causing movement of the tension cable 34 and pulley 26, as well as the articulating component 14. Once the exhaust has powered the piston 122, the exhaust is expelled from the piston chamber 126.

Figure 2:
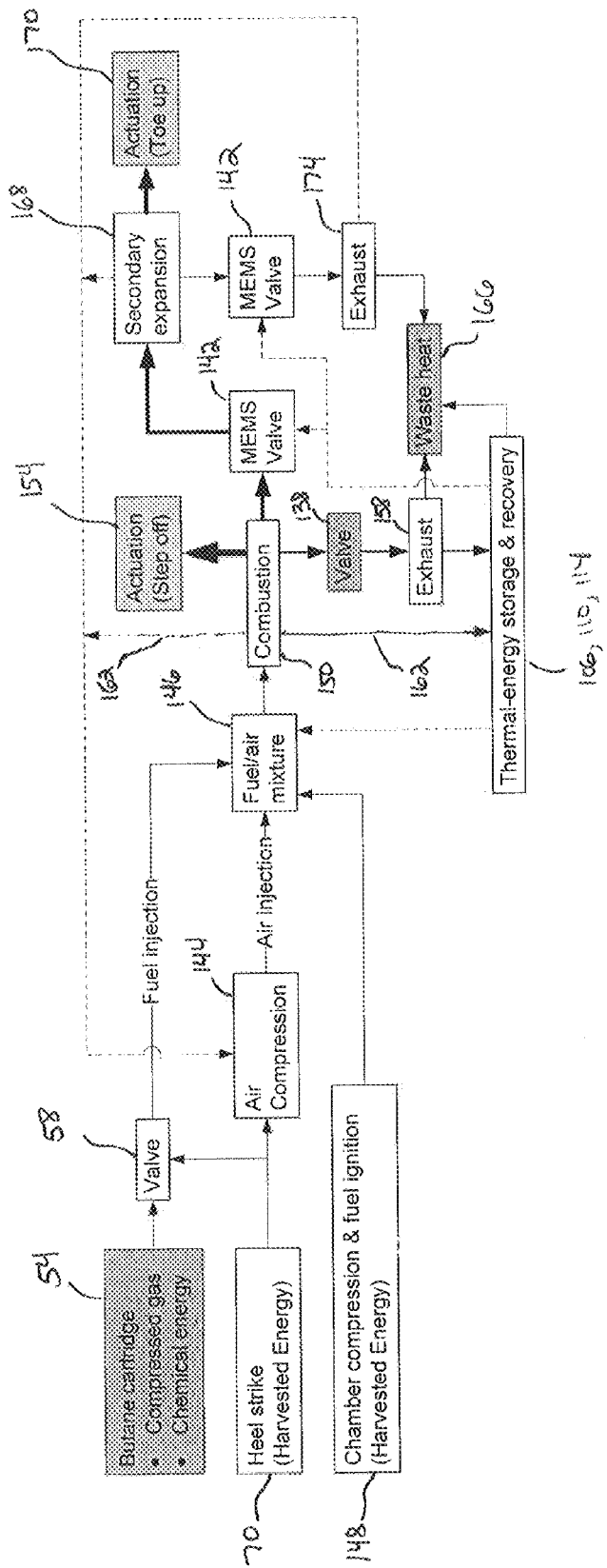
FIG. 2 is a schematic process diagram illustrating energy flow through the actuation system.

With continued reference to both FIGS. 1 and 2, the system 10 overall is an antagonistic articulated joint actuation system that moves in correlation with a gait cycle of the foot 18. The first actuator 42 provides a first, primary actuation (i.e., a "step off" or plantarflexion) and the second actuator 118 provides a secondary actuation (i.e., a "toe up" or dorsiflexion), the secondary actuation requiring less work than the primary actuation. The system 10 is also a biomimetic system, using a timed release of chemical energy for motion just as is performed by muscles, with the actuators 42, 118 taking the place of (i.e., mimicking) the muscles.

With reference to FIGS. 1 and 2, and as described above, the system 10 directs fluid from the bellows pump 70 to the air injection component 62, where the air is compressed (referenced by element 144 in FIG. 2) and then injected into the combustion chamber 46. The fluid is also directed to the bellows or bladder 82 behind the fuel cartridge 54 opening valve 58 and injecting fuel into the combustion chamber 46, thereby forming an air/fuel mixture (referenced by element 146 in FIG. 2). With reference to element 148 in FIG. 2, in some constructions, the system 10 uses harvested energy (e.g., from the bellows pump 70, or simply through movement of the foot 18 and articulating component 14), to compress the air/fuel mixture 146 within the chamber 46.

With continued reference to FIGS. 1 and 2, the compressed air/fuel mixture 146 undergoes combustion (referenced by element 150 in FIG. 2) in the chamber 46. The combustion 150 moves the piston 50, which moves the tension cable 30 and pulley 22, resulting in the first, primary actuation or "step off" (referenced by element 154 in FIG. 2). The combustion 150 also generates exhaust. Some of the exhaust (as represented by element 158 in FIG. 2), is directed through the pneumatic valve 138 and to the ambient environment or to one of the exhaust-heat recuperator 106, thermoelectric generator 110, and/or phase-change material 114, in order to store and recover energy from the exhaust 158. As illustrated in FIG. 2, this energy is then re-directed to the air/fuel mixture 146. Conduction (referenced by element 162 in FIG. 2) also occurs, which directs energy to the exhaust-heat recuperator 106, thermoelectric generator (TEG) 110, and/or phase-change material (PCM) 114, and in some constructions also back to the air injection component 62. Some waste heat (referenced by element 166 in FIG. 2) is generated from the exhaust 158 and the exhaust-heat recuperator 106, thermoelectric generator (TEG) 110, and/or phase-change material (PCM) 114.

With continued reference to FIGS. 1 and 2, the rest of the exhaust from the combustion 150 is directed through one of the valves 142 to the piston chamber 126, causing expansion in the chamber 126 (referenced as element 168 in FIG. 2) and generating the secondary actuation or "toe up" (referenced as element 170 in FIG. 2). The secondary actuation 170 is an example of exhaust energy recovery that is used in the system 10. After the secondary actuation 170 occurs, exiting exhaust (referenced as element 174 in FIG. 2) then passes through another one of the valves 142 and becomes part of the waste heat 166.

In use, the system 10 produces engine noise that is less significant than conventional engine noise, such that the system 10 is not distracting or otherwise disruptive to the user.

Figure 3:
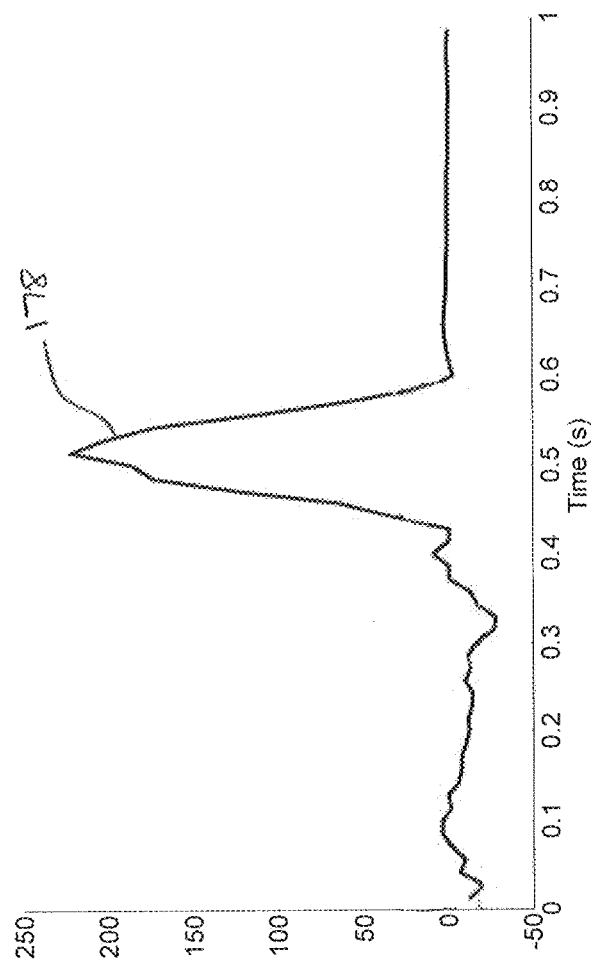
FIG. 3 is an ankle power versus time diagram illustrating an ideal power spike for a first actuation of the actuation system.
Figure 13:
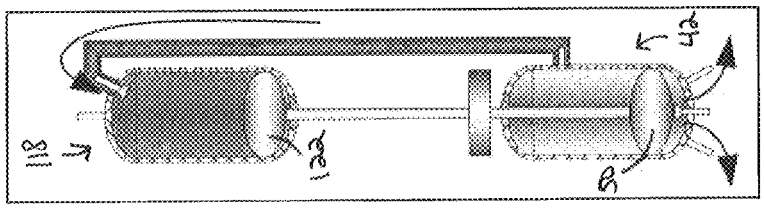
FIGS. 9-13 are schematic illustrations of an actuation system according to one construction with pistons that allow for variable diameters.
Figure 12:
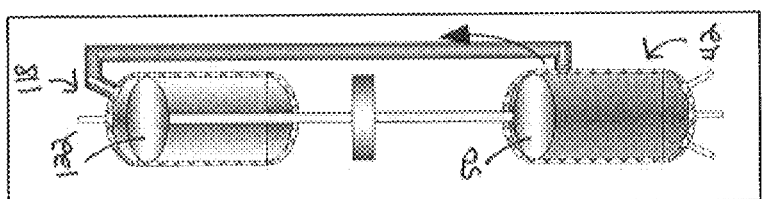
Figure 11:
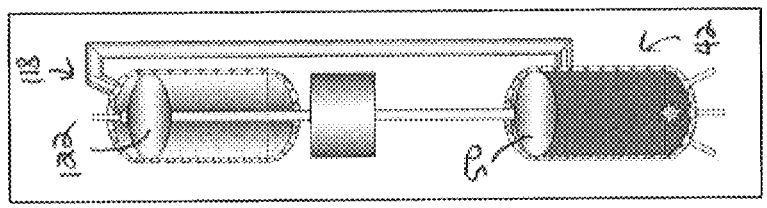
Figure 10:
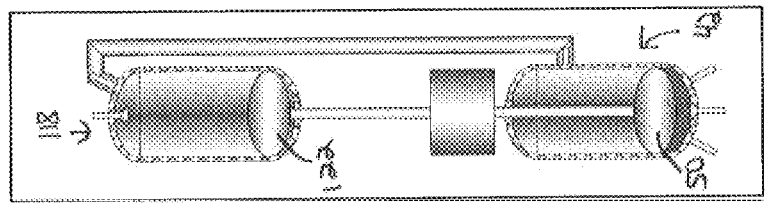
Figure 9:
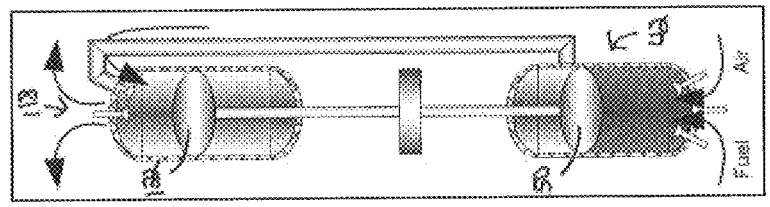
Figure 14:
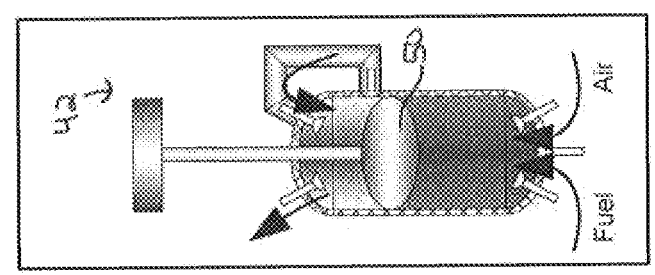
FIGS. 14-18 are schematic illustrations of an actuation system according to one construction with a single dual-acting piston.
Figure 15:
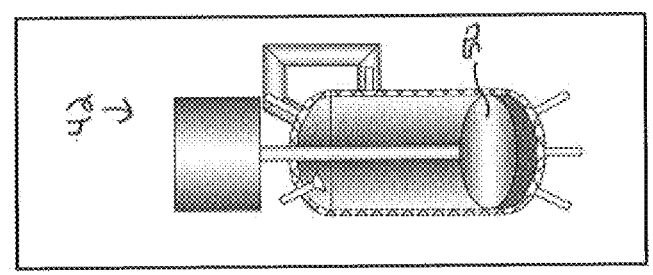
Figure 16:
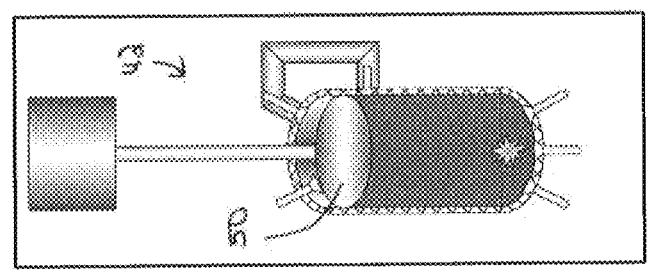
Figure 17:
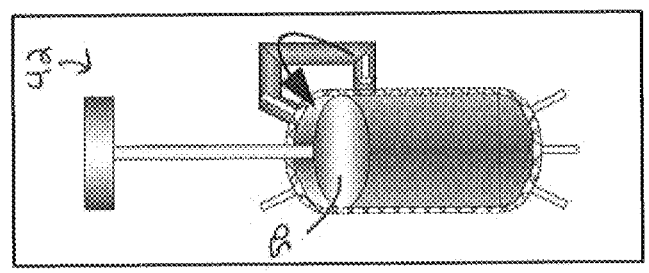
Figure 18:
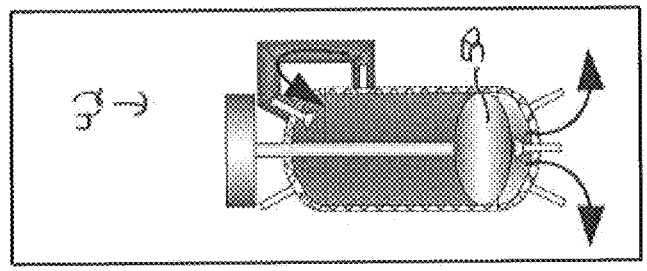

FIG. 3 illustrates ankle power versus time and an ideal power spike 178 required of the actuator 42 to duplicate the torque (i.e., the "step off" 154) of an un-impaired human. This ideal power spike is best generated by a chemical release of energy, preferably within the chamber 46 of the actuator 42. For a system 10 implemented as an orthosis, where weight is a premium, combustion of fuel provides, for example, a 500 psi minimum operating pressure to make the system 10 competitive with electric and electro-hydraulic systems that try to approximate this ideal power spike 178.

With reference to FIGS. 4-8, and as described above, the illustrated system 10 includes two pistons 50, 122 disposed in separate actuators 42, 118. The pistons 50, 122 may have variable diameters and stroke lengths (for pulley linkages like that in FIG. 2, as well as for lever-arm linkages as described further herein).

With reference to FIGS. 9-13, in some constructions the system 10 includes pistons 50, 122 that may have just variable diameters.

With reference to FIGS. 14-18, in some constructions the system 10 includes one dual-acting piston 50 (instead of two pistons) that generates both the first, primary actuation 154 and the secondary actuation 170 through re-routing of the exhaust. Multiple smaller chambers can also be used in parallel for compactness.

In some constructions, the system 10 is configured for rotary actuation (e.g., of the articulating component 14), whereas in other constructions the system 10 is configured for linear actuation of a component (e.g., a lever-arm linkage).

Figures 19, 20, 21:
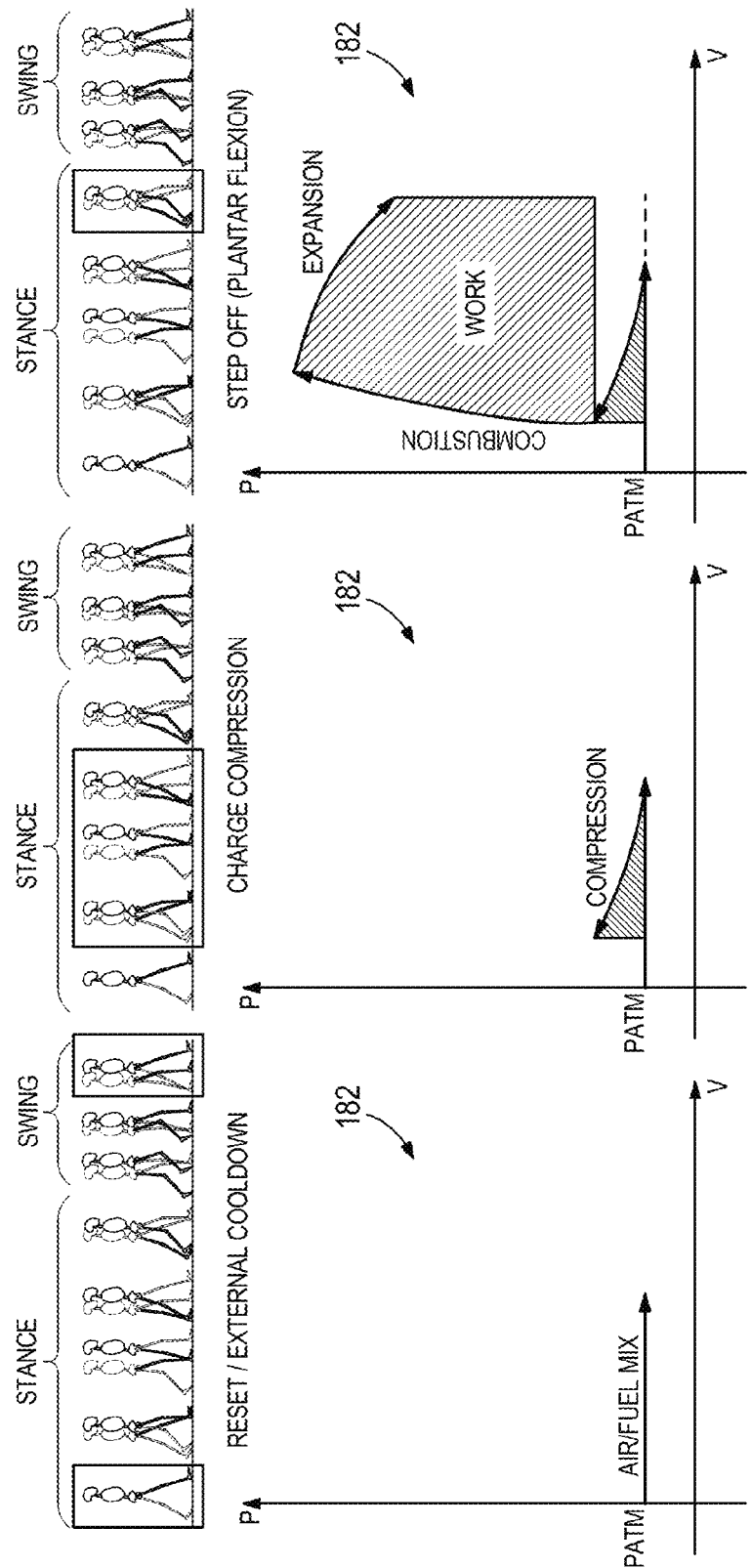

With reference to FIGS. 19-24, the system 10 includes a thermodynamic cycle 182. FIGS. 19-21 illustrate the first three stages of a preliminary portion of the cycle 182 and their relation to the gait cycle. With reference to FIG. 19, air and fuel are injected into the chamber 46. This may be accomplished with energy recovered from some exhausted fluid, or harvested with the bellows pump 70 as described above. With reference to FIG. 20, the translation of a human body's center of mass with respect to the ankle then provides a torque that can be harvested to compress the air/fuel mixture 146 in the chamber 46. There is a tradeoff here between potential energy production and hindering the gait cycle, as the chamber 46 pressure increases. The fluid does not reach the auto-ignition temperature until the end of this stage (like top-dead-center for a diesel). With reference to FIG. 21, compression or spark ignition (e.g., from the spark plug 98) initiates combustion, and subsequent expansion, of the air/fuel mixture 146 in the chamber 46, providing the first actuation 154 (i.e., the "step-off" or plantarflexion) work required.

FIGS. 22 and 23 illustrate the last two stages of the preliminary portion, and their relation to the gait cycle. With reference to FIG. 22, a division of the combustion products occurs. With reference to FIG. 23, expansion of some combustion products for the secondary actuation 170 (i.e., the "toe-up" or dorsiflexion) actuation occurs, and a remainder of the exhaust is released to the atmosphere.

Figure 24:
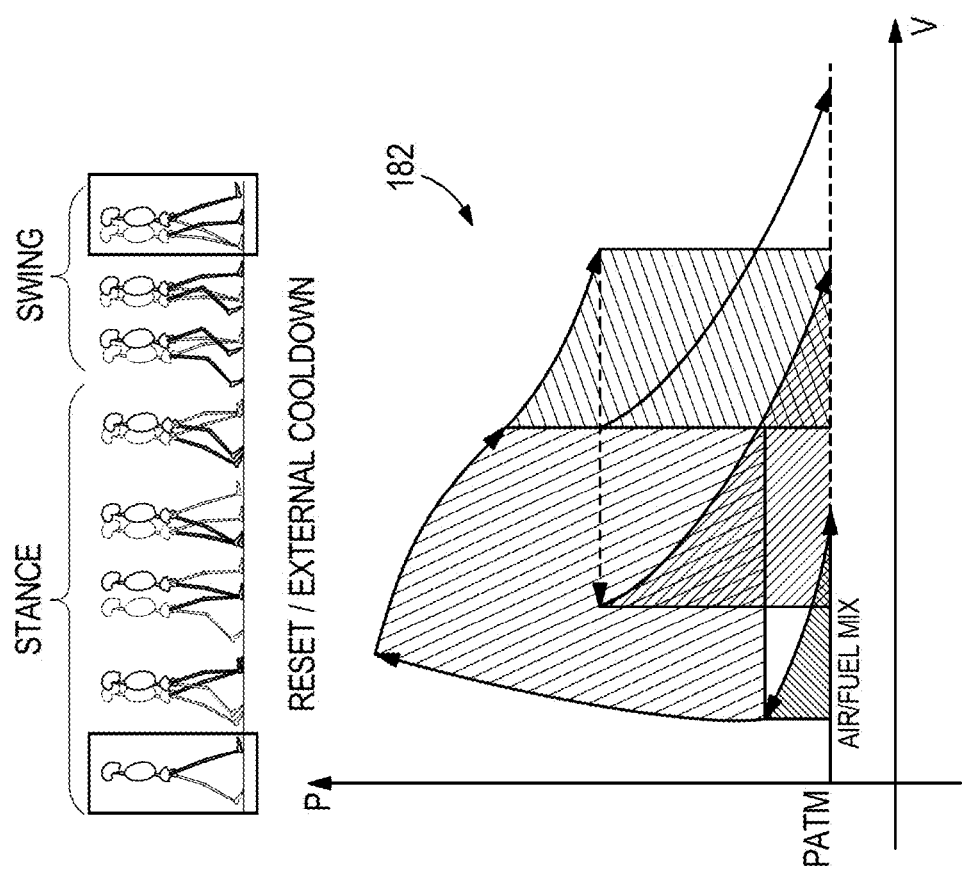

FIG. 24 illustrates a reset/external cool-down portion of the cycle 182.

While reciprocating piston engines typically have peak thermodynamic efficiencies of only 30%, a gait-matched, recuperative (co-generation) thermodynamic cycle 182 like that illustrated in FIGS. 19-24 for the system 10 provides a far greater system efficiency than current state-of-the-art pneumatic actuation systems, with a targeted minimal thermodynamic efficiency of 60%. Further, the high power-density of the system 10 leads to compact, light-weight powerplant design, increasing payload, and/or extending operation.

Figure 25:
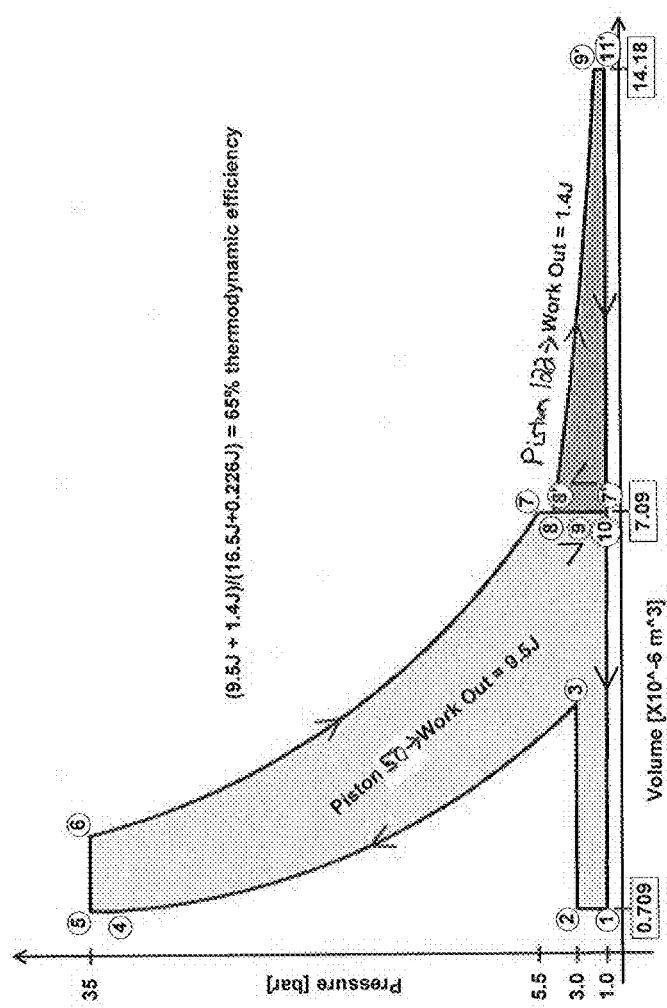
FIG. 25 is a pressure-volume diagram that relates work done by both pistons in the actuation system of FIG. 1.

With reference to FIG. 25, a pressure-volume diagram is illustrated that relates an example of work done by both the piston 50 and the piston 122. In some constructions, fifty percent of the combustion products in the primary actuator 42 are routed to the secondary actuator 118, improving thermodynamic efficiency by eight percent.

Figure 26:
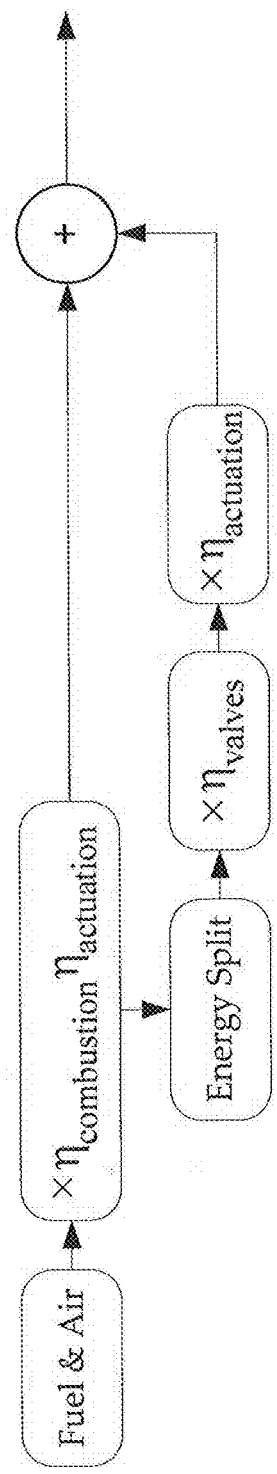
FIG. 26 is a schematic illustration of an energy-flow diagram for the actuation system of FIG. 1.

FIG. 26 schematically illustrates an energy-flow diagram for the system 10, displaying process efficiencies, and depicting energy-recovery capability.

Figure 27:
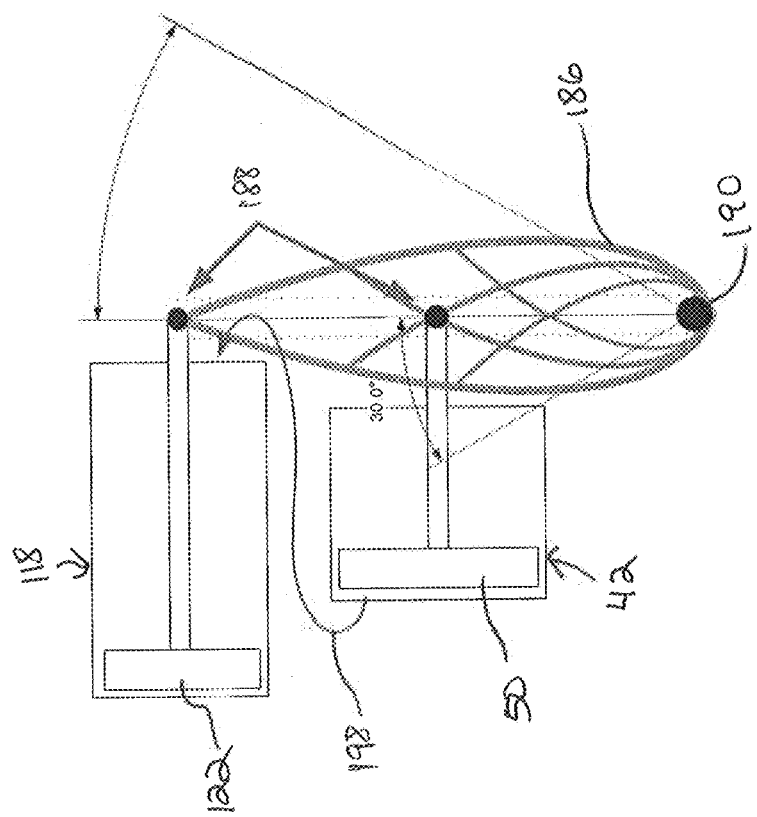
FIG. 27 is a schematic illustration of an actuation system according to one construction with a lever arm and two pistons.

With reference to FIG. 27, in some constructions the system 10 includes actuators 42, 118 that act on a lever arm 186 (as opposed to a pulley like in FIG. 1) to rotate the lever arm 186 about a pivot point or axis 190 by an angle 194, the lever arm 186 being coupled to the pistons 50, 122 at points 188 along the lever arm 186. The system 10 produces torque about the axis 190. At the end of the stroke for the lower, high-force actuator 42, exhaust gas is routed via a fluid line(s) 198 to the secondary actuator 118 for the return stroke. Here, this secondary actuator 118 is smaller in diameter, but is longer and has greater mechanical advantage. In this construction exhaust is directed into the retracting piston 50, 122 until a difference in torque is zero, wherein exhaust is then released to the atmosphere while the piston 50, 122 continues to expand.

Figure 28:
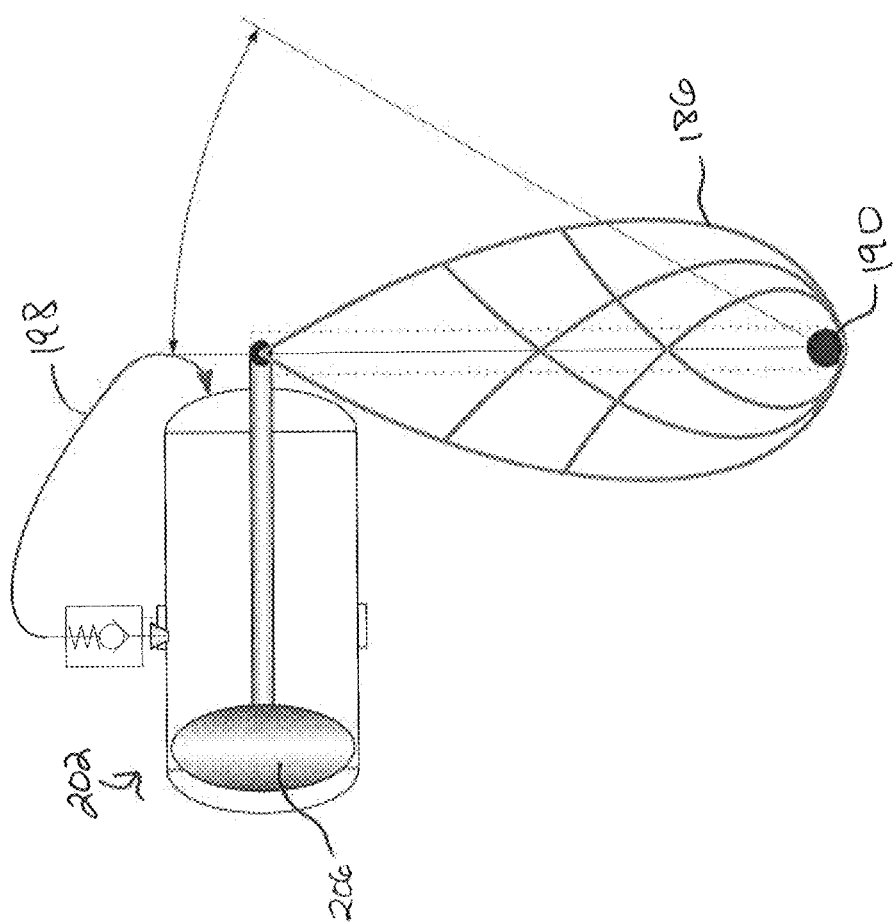
FIG. 28 is a schematic illustration of an actuation system according to one construction with a lever arm and a single dual-acting piston.

With reference to FIG. 28, in some constructions the actuators 42, 118 are embodied as a single actuator 202 with a single piston 206, so the stroke and mechanical advantage is the same for both. A common piston diameter is illustrated, but two different diameters could be used. Exhaust is moved into a back end of the piston 206 with fluid line 198 until a pressure differential is zero, wherein exhaust is then released to the atmosphere while the piston 206 continues to expand. This system 10 may use a NiTiNOL wire, for example, to activate sliding exhaust vent(s).

Figure 29:
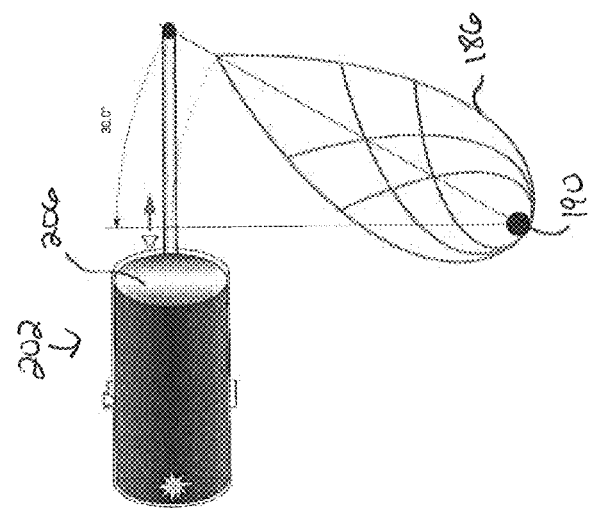

With reference to FIG. 29 (and to FIG. 21, which is the corresponding thermodynamic cycle operation), in the indicated range of the gait cycle the air/fuel mixture 146 is combusted, providing the primary torque to the articulated joint.

Figure 30:
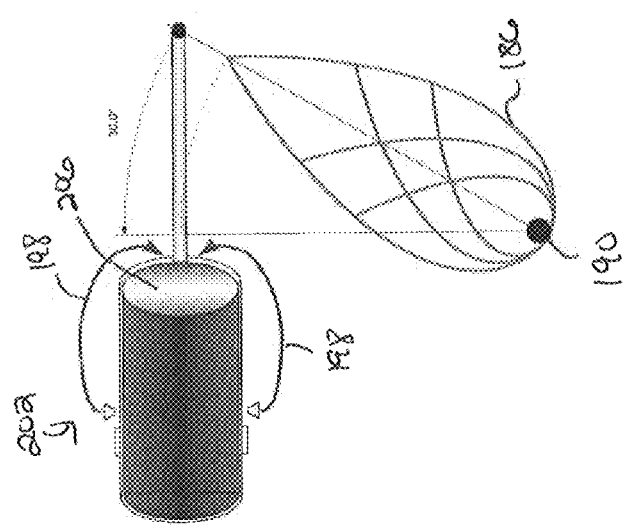

With reference to FIG. 30 (and to FIG. 22, which is the corresponding thermodynamic cycle operation), in the indicated range of the gait cycle the cylinder has reached full extension. Here, the energized gas is released, no shaft work is being done, and some thermal energy is lost. The energized gas can either be fed directly into the other end of the actuator 202 until the pressure on both sides equalizes, or held in connective fluid lines 198 at an interim pressure. The fluid lines 198 function as an accumulator and in some constructions are modified to include a "traditional" accumulator.

For increased efficiency, some of the remaining gas on the primary side may be used for air and fuel injection, either for other actuators in the system, or stored for the next cycle of originating actuator.

Figure 31:
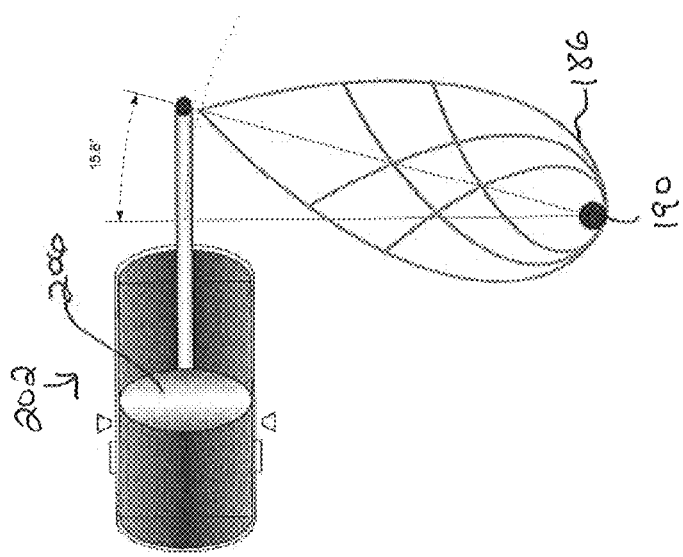
FIGS. 29-31 are schematic illustrations of the actuation system of FIG. 28 in use, the actuation system having the same thermodynamic cycle as that in FIGS. 19-24.

With reference to FIG. 31 (and to FIG. 23, which is the corresponding thermodynamic cycle operation), the energized gas has been fed directly to the other side of the actuator 202 until the pressure is equalized, and the actuator 202 has harvested a small amount of energy to move the piston 206 to an interim position. At this point, the remaining gas on the primary side is released to the atmosphere, while that on the secondary side is allowed to expand further, providing additional shaft work, in the opposite direction from the primary side.

Figure 32:
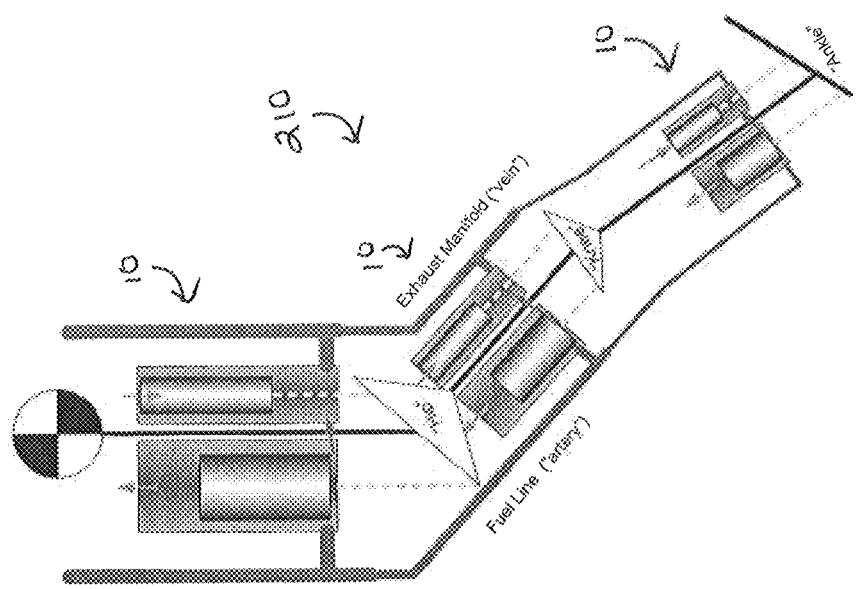
FIGS. 32 and 33 are schematic illustrations of a plurality of the actuation systems of FIG. 1 as used on a human or biomimetic-robot leg.
Figure 33:
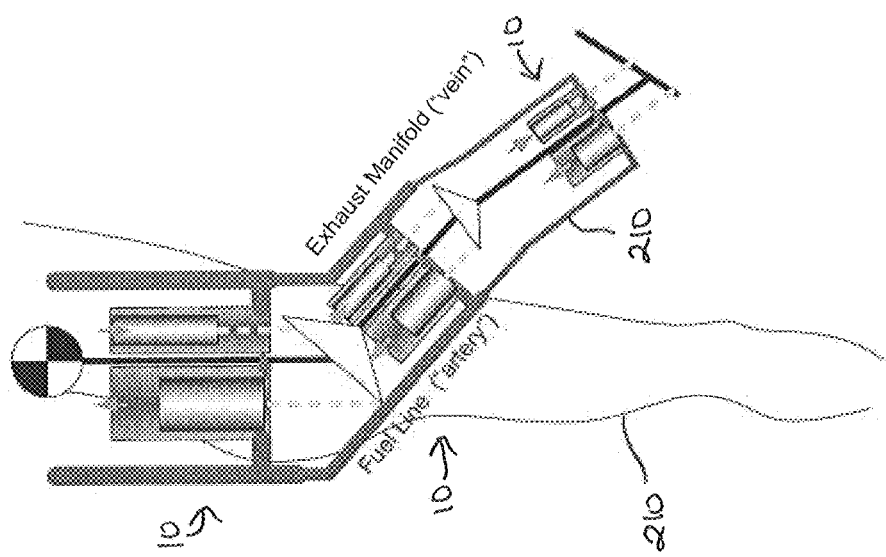

The actuation systems described above provide asymmetric, antagonistic articulated-joint actuation. While the actuation system 10 is illustrated in the context of an orthosis device for a human foot 18, in other constructions the articulation system 10 is used on other joints and appendages, including but not limited to arms, elbows, hips, etc., and/or is used in combination with other similar systems 10. For example, and with reference to FIGS. 32 and 33, in some constructions multiple systems 10 (or a single system 10 with numerous actuators coupled together) are used on a human leg 210. The systems 10 define a human-assistive exoskeleton, and assist in walking and/or running The fuel supply and exhaust routing in these systems 10 can be made similar to the vasculature of organic systems. Fuel may act as a thermal-energy transport (e.g., to transport out waste heat to prevent overheating, or to transfer in heat). In some constructions the fuel may be mixed with other fluid coolant, and separated locally for actuation.

In some constructions, the actuation system 10 is used not as an orthosis device, but rather as a full replacement for the joint or appendage (i.e., as a prosthetic).

Figure 34:
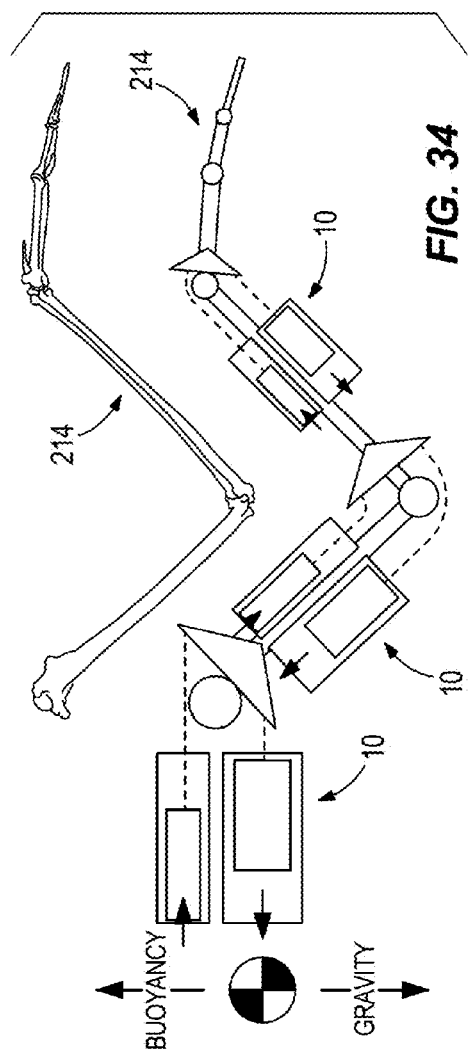
FIGS. 34 and 35 are schematic illustrations of a plurality of the actuation systems of FIG. 1 as used on animal or animal-like (biomimetic) robot non-leg appendages (e.g., fins or wings).
Figure 35:
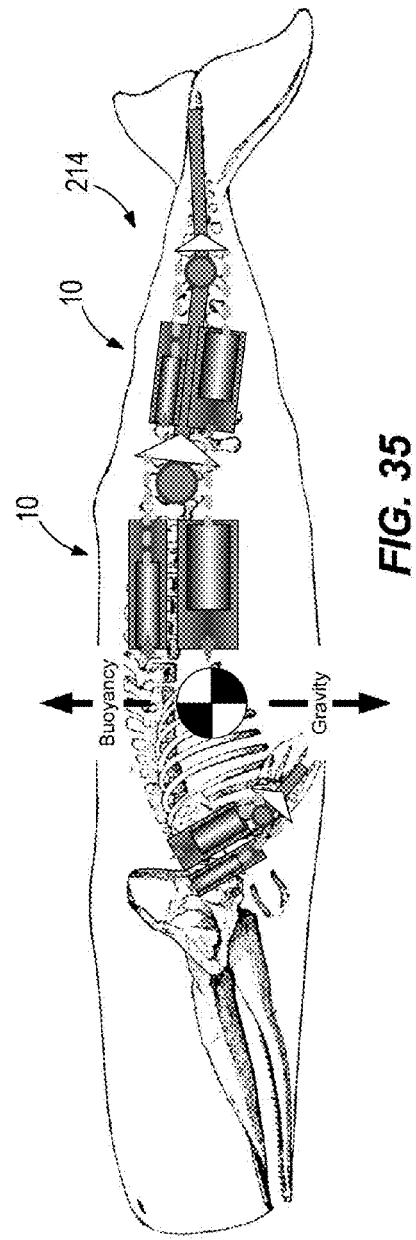

With reference to FIGS. 34 and 35, in some constructions the actuation system 10 is used on non-human joints and appendages. For example, in some constructions the actuation system 10 is used on animal and animal-like (biomimetic) robot joints or appendages 214 (e.g., legs, wings, tails) to provide assistance and movement to animal joints and appendages, and to utilize cycles (e.g., gait cycles) associated with such joints and appendages. In some constructions the system 10 is used underwater, to assist in swimming gait cycles, or in the assistance of flying. In some constructions exhaust gases are used for ballast and buoyancy control, manipulating a center of gravity as desired. When surrounded by fluid and not in contact with ground, the balance between buoyancy and gravity can help to drive the system 10. With reference to FIG. 34, for example, a main body of a wing appendage 214 can have its buoyancy reduced after primary actuation, and as it falls, the higher drag on the wing appendage 214 can be used to compress the air/fuel mixture 146 for the next downward propulsion stroke. In some constructions compressed-gas stores may provide an air/fuel-compression energy for takeoff, and other bursts of energy as needed. Exhaust gases from the system may replenish this source.

In yet other constructions the system 10 is used in conjunction with one or more other actuations systems 10 to form an entire robot or other mechanical structure that is capable of various degrees of articulated movement and gait cycles.

The system 10 described herein provides efficient, high-torque, light-weight, compact locomotion in the gait cycle. A portion of the residual thermal energy contained within the acting fluid for the "power stroke" (e.g., plantarflexion) of the gait cycle is recovered to drive the "return stroke" (e.g., dorsiflexion) and to provide asymmetric, antagonistic actuation of an articulated joint. Energy recovery (i.e., through using the exhaust from the primary actuator 42 to power the second actuator 118) significantly improves the efficiency of the system and the charging of the fluid through chemical-energy release affords higher torques (greater power density).

The highly-energized fluid to be exhausted at the end of the "step-off" (plantarflexion) phase of the gait cycle is used for the secondary actuation phase "toe-up" (dorsiflexion) that requires significantly less power. This energy recovery increases the efficiency of the actuator's operation.

The energy density of hydrocarbons in the system 10 remains much higher than that of battery cells, allowing for more compact and lighter-weight designs. Additionally, the energy is employed as completely as possible. As described above, butane is one type of fuel that may be used with the system 10. Butane is advantageous because it burns cleanly, and is readily available in refillable cartridges 54. The low fuel-consumption rate of the system 10 means that the emissions of $CO_2$ are also low, comparable to that produced by the muscles themselves.

Other energy sources aside from fuel combustion with butane or other fuels (e.g., natural methane gas) include compressed gas tanks and catalytic decomposition (e.g., $H_2O_2$ (chemofluidics)).

Although the invention has been described in detail with reference to certain preferred embodiments, variations and modifications exist within the scope and spirit of one or more independent aspects of the invention as described.

What is claimed is:

1. An actuation system for a joint comprising:
an actuator including a piston;
an articulating element coupled to the actuator that is driven by the piston to match a gait cycle of an appendage;
an energy source engaged with the piston that energizes working fluid within the actuator to drive the piston and generate exhaust gas;
a plurality of valves coupled to the actuator; and
an exhaust gas holding element coupled to the actuator that is sized to hold a volume of the exhaust gas contained within the actuator.

2. The actuation system of claim 1, wherein the articulating element includes a torsion element.

3. The actuation system of claim 2, wherein the torsion element includes a radius that varies about an axis.

4. The actuation system of claim 1, wherein the articulating element includes a linear-force element.

5. The actuation system of claim 1, wherein the articulating element includes a first pulley, a second pulley, and tension cables coupled to the first and second pulleys, one of the tension cables extending between the actuator and the first pulley, and another of the tension cables extending between the exhaust gas holding element and the second pulley.

6. The actuation system of claim 1, wherein the piston is a dual-acting piston, and the exhaust gas holding element is a back side of the first actuator piston.

7. The actuation system of claim 1, wherein the actuator is a first actuator and the piston is a first piston, and wherein the exhaust gas holding element is a second actuator that includes a second piston.

8. The actuation system of claim 7, wherein the first and second actuators are opposing-action piston engines that harvest energy from one another's generated exhaust.

9. The actuation system of claim 1, wherein the energy source is selected from a group consisting of a fuel, a catalytic decomposition, and a compressed gas.

10. The actuation system of claim 1, wherein the plurality of valves includes air and fuel injection valves that control movement of air and fuel into the actuator, as well as an exhaust valve controls movement of exhaust into the exhaust gas holding element.

11. The actuation system of claim 1, further comprising a heel-strike energy-harvesting hydraulic bellows pump coupled to the actuator.

12. The actuation system of claim 11, wherein the actuator includes a fuel injector and an air injector, and wherein the bellows pump actuates the fuel injector and the air injector to inject fuel and air into the actuator when the bellows pump is compressed.

13. The actuation system of claim 1, further comprising a piezoelectric spark generator coupled to the actuator that ignites a mixture of air and fuel within the actuator.

14. A method of using an actuation system for a joint comprising:
coupling an actuation system to an appendage, the actuation system including a primary actuator and a secondary actuator, the primary and secondary actuators working in dual, opposing motion to one another as the appendage moves through a gait cycle;
moving a piston within the primary actuator to generate a first actuation movement of an articulating element coupled to the primary actuator;
directing exhaust into the second actuator to power a second actuation movement of the articulating element; and
matching the gait cycle of the appendage with a thermodynamic cycle of the actuation system.

15. The method of claim 14, further comprising generating a spark with a piezoelectric spark generator through movement of the appendage, and igniting a mixture of air and fuel within the primary actuator with the spark.

16. The method of claim 14, further comprising igniting a mixture of air and fuel within the primary actuator via compression ignition.

17. The method of claim 14, further comprising injecting air and fuel into the primary actuator with a hydraulic bellows pump.

18. The method of claim 14, wherein the first actuation movement includes plantarflexion of a foot and the second actuation movement includes dorsiflexion of the foot.

19. The method of claim 14, further comprising using energy from the exhaust gas to power actuation elements on other actuation systems.

20. The method of claim 14, further comprising using a thermo-electric generator to power valves.

21. The method of claim 14, wherein the step of moving the piston includes energizing of working fluid within the actuation system by an exothermic reaction within the actuation system.

22. The method of claim 14, wherein the step of moving the piston includes compressing an air/fuel mixture with fluid drag.

23. The method of claim 14, further comprising coupling additional actuation systems to the actuation system such that the combination of a fuel supply and exhaust for the combined actuation systems is similar to an organic vasculature, and the fuel supply is a thermal-energy transport.

24. A method of harvesting energy with an actuation system for a joint comprising:
coupling an actuation system to an appendage, the actuation system including a primary actuator powered by a mixture of air and fuel;
pressing a portion of the appendage toward a surface to engage and activate a hydraulic bellows on the actuation system; and
injecting air and fuel into the primary actuator with the activated hydraulic bellows.

25. The method of claim 24, wherein the hydraulic bellows is disposed below a heel when the actuation system is coupled to a foot.

26. The method of claim 24, further comprising generating a spark with a piezoelectric spark generator through movement of the appendage, and igniting a mixture of air and fuel within the primary actuator with the spark.

* * * * *